United States Patent [19]

Tanaka et al.

[11] Patent Number: 4,772,587

[45] Date of Patent: Sep. 20, 1988

[54] DIPEPTIDE DERIVATIVE OF FATTY ACID

[75] Inventors: Takaharu Tanaka; Naoki Higuchi; Masayuki Saitoh; Masaki Hashimoto, all of Osaka, Japan

[73] Assignee: Suntory Limited, Osaka, Japan

[21] Appl. No.: 852,709

[22] Filed: Apr. 16, 1986

[30] Foreign Application Priority Data

Apr. 16, 1985 [JP] Japan .................................. 60-80872
Oct. 9, 1985 [JP] Japan ................................. 60-225499

[51] Int. Cl.$^4$ ..................... A61K 37/02; C07D 207/00
[52] U.S. Cl. ......................................... 514/19; 514/18; 514/359; 514/408; 514/423; 530/323; 530/331; 530/332
[58] Field of Search ....................... 530/331, 323, 332; 514/18, 19, 359, 408, 423; 548/535

[56] References Cited

FOREIGN PATENT DOCUMENTS 60-188317 6/1985 Japan.
60-172929 8/1985 Japan.

OTHER PUBLICATIONS

The Proceedings of 1984 Annual Meeting, pp. 752–754.
Nakamura et al, "The Monomolecular Films of U-Palmitoyl-L-Proline Oligomers" *J. of Coll. and Interface Science*, vol. 61, No. 1, 1977, pp. 86–94.
"Inhibition of Rabbit Brain Prolyl Endopeptidase by N-Benzyloxy-Carbonyl-Prolyl-Prolinal, A Transition State Aldehyde Inhibitor", *Journal of Neurochemistry*, vol. 41, No. 1, 1983, pp. 69–75.

*Primary Examiner*—Delbert R. Phillips
*Assistant Examiner*—Nathan M. Nutter
*Attorney, Agent, or Firm*—Cushman, Darby & Cushman

[57] ABSTRACT

A novel compound that exhibits inhibitory activity against prolyl endopeptidase and a method for chemical synthesis of said compound, as well as its use as a prolyl endopeptidase inhibitor and an anti-amnesic agent that contains said compound as the active ingredient are provided.

6 Claims, No Drawings

DIPEPTIDE DERIVATIVE OF FATTY ACID

BACKGROUND OF THE INVENTION

The present invention relates to a novel compound that exhibits enzyme inhibiting activity against prolyl endopeptidase (EC, 3.4.21.26). The invention also relates to a method for chemical synthesis of such novel compounds, as well as its use as a prolyl endopeptidase activity inhibitor and a drug, especially an anti-amnesic agent, that contains it as the active ingredient.

Prolyl endopeptidase is known to inactivate neurotransmitters such as Substance P, thyrotropin-releasing hormone (TRH) and neurotensin, or vasopressin speculatively associated with memory. Tsuru and Yoshimoto of the Department of Pharmaceutical Sciences, Nagasaki University, found that compounds capable of inhibiting the prolyl endopeptidase activity were effective for preventing experimental amnesia caused in rats by scopolamine. Based on this discovery, they suggested the potential use of prolyl endopeptidase activity inhibitors as anti-amnesic agents.

SUMMARY OF THE INVENTION

Motivated by the report of Tsuru and Yoshimoto, the present inventors made various efforts to find novel compounds that exhibited strong inhibiting activity against prolyl endopeptidase as well as anti-amnesic activity and which yet had satisfactorily low toxicity levels. As a result, the inventors have synthesized compounds which are close to natural substances by a combination of fatty acids, which enjoy a high safety level as natural compounds, and amino acids or peptide compounds, and found that novel compounds with anti-prolyl endopeptidase activity and having the general formula (I) shown below exhibited excellent effects against amnesia. The present invention has been accomplished on the basis of this finding.

DETAILED DESCRIPTION OF THE INVENTION

The dipeptide derivative of fatty acid of the present invention is represented y the general formula (I):

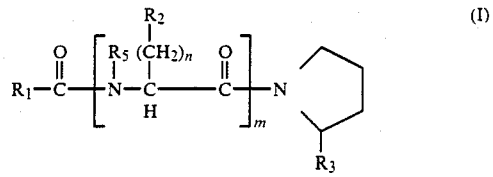

(wherein m is an integer of 0, 1 or 2; n is an integer of 0 to 12; $R_1$ is a saturated or unsaturated unbranched hydrocarbon group having 5 to 25, preferably 10 to 20, most preferably 15 to 17 carbon atoms (the unsaturated carbon chain may include a plurality of double bonds); $R_3$ is a lower alkylester group of the formula: $-COOR_4$ (wherein $R_4$ is a lower alkyl group) or hydroxymethyl group or formyl group; $R_2$ represents, when n is 0, an unbranched or branched alkyl group having 1 to 5 carbon atoms, whereas, when n is an integer of 1 to 12, $R_2$ is methyl group, phenyl group, hydroxyphenyl group, carboxyl group, formyl group, amino group, hydroxy group or methylthio group (these groups may be substituted); $R_5$ is hydrogen atom, or when n is 3, $R_2$ and $R_5$ together may represent a single bond between carbon atom and nitrogen atom).

In formula (I), when n represents an integer of 1 or more, it is preferably 1 to 12, more preferably 1 to 6.

The compounds of formula (I) in which $R_2$ and $R_5$ together form a single bond between carbon atom and nitrogen atom have the formula (Ib):

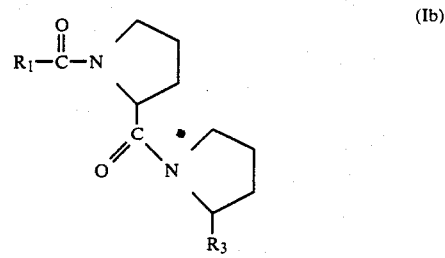

The compounds of formula (I) differ greatly from the known piracetam derivative based anti-amnesic agents in that the former contains a proline residue and an unbranched fatty acid chain. Because they are amino acid or peptide derivatives, the compounds of formula (I) present extremely low toxicity levels in organisms.

The following compounds of formula (I) are particularly preferred because of their high anti-prolyl endopeptidase activities (the follow compounds may be sometimes referred to by the numbers in parentheses, hereinafter):

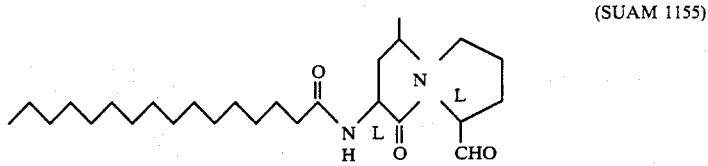

(SUAM 1155)

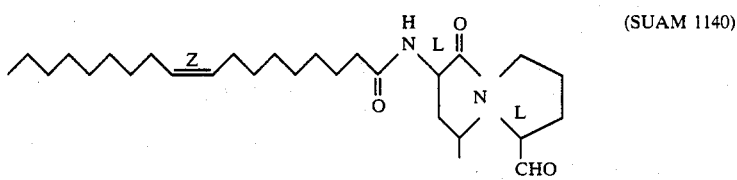

(SUAM 1140)

-continued
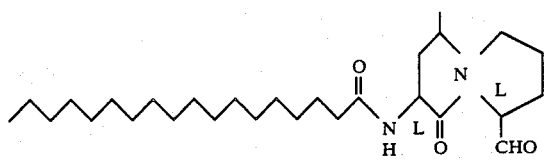
(SUAM 1154)
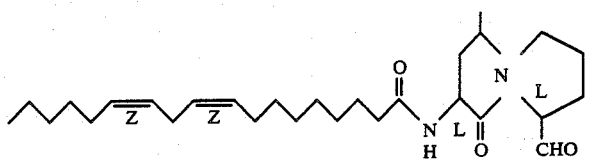
(SUAM 1157)
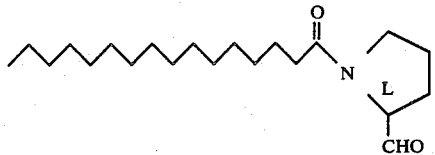
(SUAM 1139)
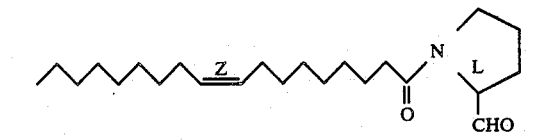
(SUAM 1134)
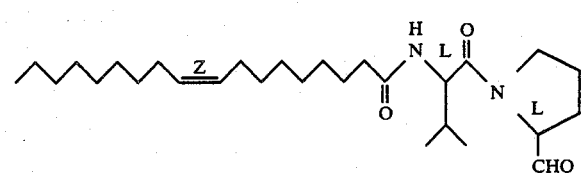
(SUAM 1156)
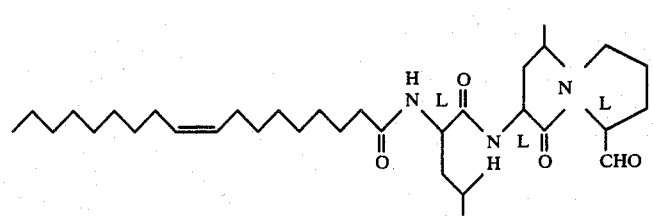
(SUAM 1158)
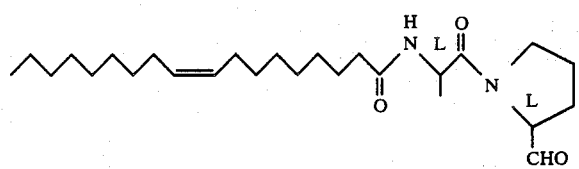
(SUAM 1092)
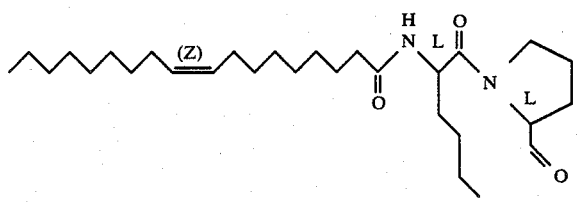
(SUAM 1166)
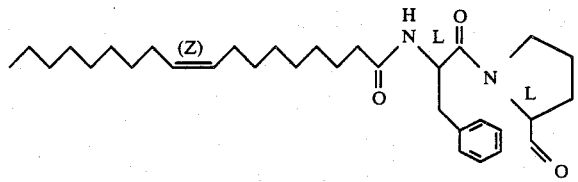
(SUAM 1212)

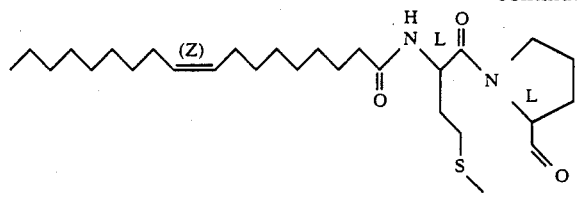 (SUAM 1214)

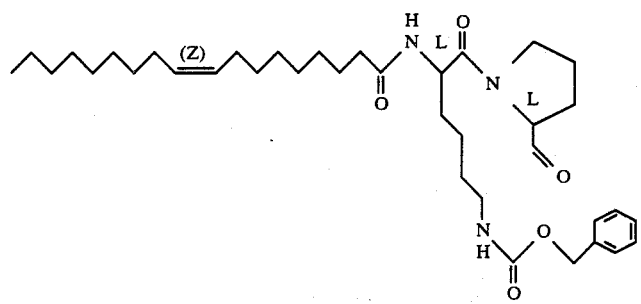 (SUAM 1216)

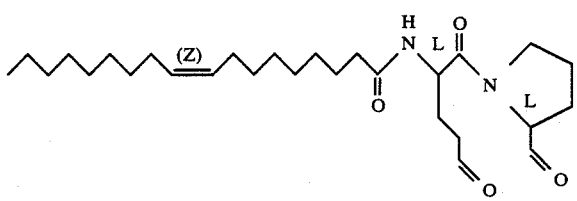 (SUAM 1217)

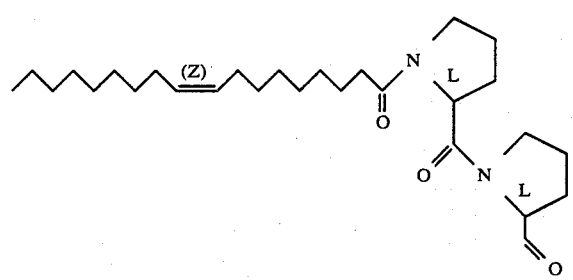 (SUAM 1215)

The compounds of the present invention may be synthesized by any of the conventional methods of peptide synthesis, but they may be conveniently synthesized by the following procedures in accordance with the present invention, in which each of the abbreviations represents the following meanings:

Z: benzyloxycarbonyl group
Boc: t-butyloxycarbonyl group
Pro: proline residue
Ala: alanine residue

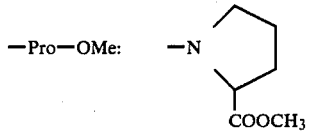

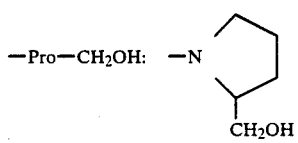

norLeu: norleusin residue
Phe: phenylalanine residue
Met: methionine residue
Lys: lysine residue
Val: valine residue
Leu: leusin residue
Lys(Z): N$^\epsilon$-benzyloxycarbonyl lysine residue
Glu(Bzl): glutamic acid-$\gamma$-benzylester residue

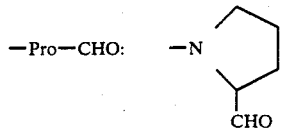

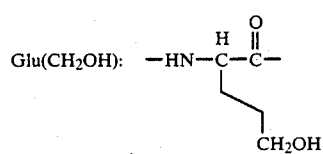

Glu(CHO): 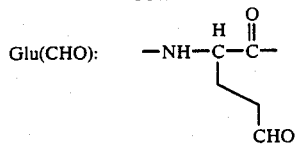

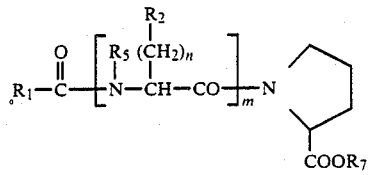

OMe: methylester residue
WSCD: N-ethyl-N'-N'-dimethylaminopropyl carbodiimide
TEA: triethylamine The compounds of formula (I) of the present invention may be synthesized by the following procedures:

If the compounds have a lower alkyl ester group as $R_3$ in formula (I) and are expressed by the formula (Id):

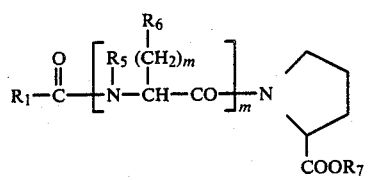

(wherein m is an integer of 0, 1 or 2; n is an integer of 0 to 12; $R_1$ is a saturated or unsaturated unbranched organic group having 5 to 25 carbon atoms (the unsaturated carbon chain may include a plurality of double bonds); $R_7$ is a lower alkyl group; $R_6$ represents, when n is 0, an unbranched or branched alkyl group having 1 to 5 carbon atoms, whereas, when n is an integer of 1 to 12, $R_6$ is methyl group, phenyl group, hydroxyphenyl group whose hydroxyl group is protected, protected carboxyl group, protected amino group, protected hydroxyl group or methylthio group; $R_5$ is hydrogen atom, or when n is 3, $R_6$ and $R_5$ together may represent a single bond between carbon atom and nitrogen atom), they may readily be synthesized by any of the conventional methods from carboxylic acid, acid anhydride or carbonyl chloride of the formula:

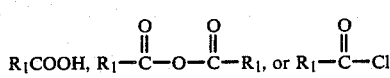

(wherein $R_1$ is a saturated or unsaturated unbranched organic group having 5 to 25 carbon atoms (the unsaturated carbon chain may include a plurality of double bonds)), and peptide or amino acid having a proline residue, whose carboxyl group has been converted to a lower alkylester, of the formula (II):

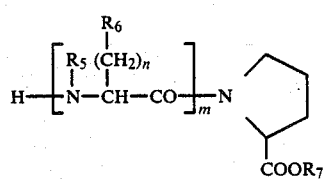

(wherein $R_5$, $R_6$, $R_7$, n and m are as defined above).

The protected groups of the compounds of formula (Id) are removed by any of the known methods in relation to amino acid or peptide, so as to obtain dipeptide derivative of fatty acid of the present invention represented by the formula (Ie)

(wherein $R_1$, $R_2$, $R_5$, $R_7$, n and m are as defined above).

Methanol is added dropwise to a mixture of the compound of formula (Id) and sodiumborohydride suspended in t-butyl alcohol or tetrahydrofurane, so as to reduce the compound, thereby obtaining a compound (If) which has hydroxymethyl group converted from the carboxyl group:

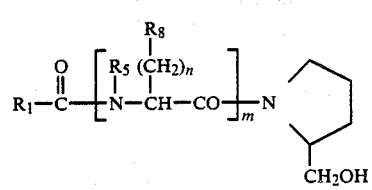

(wherein $R_1$, $R_5$, n and m are as defined above; when n is 0, $R_8$ is an unbranched or branched alkyl group having 1 to 5 carbon atoms whereas, when n is an integer of 1 to 12, $R_8$ is methyl group, phenyl group, hydroxyphenyl group whose hydroxyl group is protected, protected amino group, protected hydroxyl group, hydroxyalkyl group whose hydroxyl group is protected, methylthio group or hydroxymethyl group, or when n is 3 $R_8$ and $R_5$ together may represent a single bond between carbon atom and nitrogen atom).

The compound of formula (If) is subjected to a deprotect raction commonly used in the field of amino acid and peptide, so as to obtain dipeptide derivative of fatty acid of the present invention having the formula (Ig):

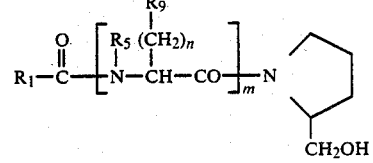

(wherein $R_1$, $R_5$, n and m are as defined above, when n is 0, $R_9$ is an unbranched or branched alkyl group having 1 to 5 carbon atoms, whereas, when n is an integer of 1 to 12, $R_9$ is methyl group, phenyl group, hydroxyphenyl group, amino group, hydroxyl group, hydroxymethyl group or methylthio group, or when n is 3, $R_9$ and $R_5$ together may represent a single bond between carbon atom and nitrogen atom).

The compound of formula (If) is oxidized so as to obtain dipeptide derivative of fatty acid represented by the formula (Ih):

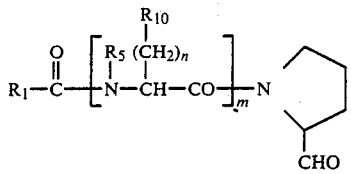

(wherein $R_1$, $R_5$, n and m are as defined above; $R_{10}$ represents, when n is 0, an unbranched or branched alkyl group having 1 to 5 carbon atoms, whereas, when n is an integer of 1 to 12, $R_{10}$ is methyl group, phenyl group, hydroxyphenyl group whose hydroxyl group is protected, protected amino group, protected hydroxyl group, hydroxyalkyl group whose hydroxyl group is protected, methylthio group or formyl group, or when n is 3, $R_{10}$ and $R_5$ together may represent a single bond between carbon atom and nitrogen atom).

In this oxidation, it is most preferable to employ sulfur trioxide-pyridine complex as an oxydizing agent. A suitable reaction solvent is dimethyl sulfoxide and the reaction may be carried out at room temperature. A period of about 1 hour will be sufficient. The compound (Ih) is subjected to the same de-protect reaction as that mentioned above so as to obtain dipeptide derivative of fatty acid represented by the fomula (Ii):

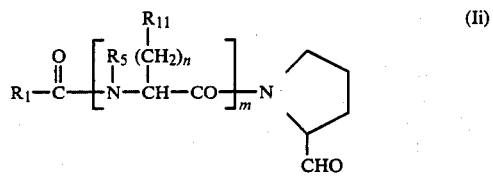

(wherein $R_1$, $R_5$, n and m are as defined above, $R_{11}$ represents, when n is 0, an unbranched or branched alkyl group having 1 to 5 carbon atoms, whereas, when n is an integer of 1 to 12, $R_{11}$ is methyl group, phenyl group, hydroxyphenyl group, amino group, hydroxyl group, hydroxyalkyl group, methylthio group or formyl group, or when n is 3, $R_{11}$ and $R_5$ together may represent a single bond between carbon and nitrogen atom).

The present invention is hereinunder described in greater detail by way of an Example for Reference and Practical Examples.

EXAMPLE FOR REFERENCE

Synthesis of startinq comoound represented by formula (II):

(a) H-Ala-Pro-OMe

Z-Ala-OH (1 equivalent), Pro-OMe hydrochloride (1 equivalent) and TEA (1 equivalent) were dissolved in dry methylene chloride, and WSCD (1 equivalent) was added under cooling with ice. Thereafter, the mixture was stirred at room temperature for 20 hours, and the reaction mixture was washed successively with 1N HCl, water, saturated aqueous sodium bicarbonate, water and saturated brine. After drying over anhydrous magnesium sulfate, the solvent was distilled off under vacuum. The resulting crude product was purified by medium-pressure liquid column chromatography on silica gel. The obtained Z-Ala-Pro-OMe (1 equivalent) was dissolved in ethanol, and boron trifluoride-ether complex (1 equivalent) and palladium on carbon (a small amount) were added. The mixture was subjected to catalytic reduction to remove the Z group, and the solvent was distilled off under vacuum to obtain the end compound.

Instead of Z-Ala-OH, (a) Z-Val-OH, (b) Z-Leu-OH, (c) Z-Phe-OH, (d) Z-Met-OH and (e) Z-norLeu-OH were used as starting compounds to obtain (a') H-Val-Pro-OMe, (b') H-Leu-Pro-OH, (c') H-Phe-Pro-OH, (d') H-Met-Pro-OMe and (e') H-norLeu-Pro-OMe as oils, respectively.

(b) H-Lys(Z)-Pro-OMe trifluoroacetate

Boc-Lys(Z)-OH (1 equivalent), Pro-OMe hydrochloride (1 equivalent) and TEA (1 equivalent) were dissolved in dry methylene chloride, and WSCD (1 equivalent) was added under cooling with ice. Thereafter, the mixture was stirred at room temperature for 20 hours, and the reaction mixture was washed successively with 1N HCl, water, saturated aqueous sodium bicarbonate, water and saturated brine. After drying over anhydrous magnesium sulfate, the solvent was distilled off under vacuum. The resulting crude product was purified by medium-pressure liquid column chromatography on silica gel to obtain the end compound. Boc-Lys(Z)-Pro-OMe (1 equivalent) thus obtained was dissolved in dry methylene chloride, and an excess of trifluoroacetic acid was added. The mixture was stirred (for about 6 hours), and the solvent was distilled off under vacuum to obtain the end compound (oil).

Instead of Boc-Lys(Z)-OH in (b), Boc-Glu(Bzl)-OH was used as a starting compound to obtain H-Glu(Bzl)-Pro-OMe trifluoroacetate (oil).

(c) H-Leu-Leu-Pro-OMe

Z-Leu-OH (1 equivalent), H-Leu-Pro-OMe (1 equivalent) synthesized in (a) and TEA (1 equivalent) were dissolved in dry methylene chloride, and WSCD (1 equivalent) was added under cooling with ice. Thereafter, the mixture was stirred at room temperature for 20 hours, and the reaction mixture was washed successively with 1N HCl, water, saturated aqueous sodium bicarbonate, water and saturated brine. After drying over anhydrous magnesium sulfate, the solvent was distilled off under vacuum. The resulting crude product was purified by medium-pressure liquid column chromatography to obtain the end compound. Z-Leu-Leu-Pro-OMe (1 equivalent) thus obtained was dissolved in ethanol, and boron trifluoride-ether complex (1 equivalent) and palladium on carbon (a small amount) were added. The mixture was subjected to catalytic reduction in a hydrogen atmosphere to remove the Z group, and the solvent was distilled off under vacuum to obtain the end compound as an oil.

(d) H-Pro-Pro-OMe

Z-Pro-OH (1 equivalent), H-Pro-OMe hydrochloride (1 equivalent) and TEA (1 equivalent) were dissolved in dry methylene chloride, and WSCD (1 equivalent) was added under cooling with ice. Thereafter, the mixture was stirred at room temperature for 20 hours, and the reaction mixture was washed successively with 1N HCl, water, saturated aqueous sodium bicarbonate, water and saturated brine. After drying over anhydrous magnesium sulfate, the solvent was distilled off under vacuum. The resulting crude product was purified by medium-pressure liquid column chromatography on silica gel to obtain the end compound. Z-Pro-Pro-OMe (1 equivalent) thus obtained was dissolved in ethanol, and boron trifluoride-ether complex (1 equivalent) and palladium on carbon (a small amount) were added. The mixture was subjected to catalytic reduction in a hydrogen atmosphere to remove the Z grup, and the solvent was distilled off under vacuum to obtain the end compound as an oil.

EXAMPLE 1

(a) N-oleoyl-Pro-OMe (SUAM 1131)

H-Pro-OMe hydrochloride (1 equivalent) and TEA (2 equivalents) were dissolved in dry tetrahydrofurane, and oleoyl chloride (1 equivalent) was added dropwise under cooling with ice. Thereafter, the mixture was stirred at room temperature for 6 hours, and the hydrochloride of TEA separated out was filtered off. The solvent was distilled off under vacuum, and the resulting crude product was dissolved in a small amount of ether. Thereafter, the mixture was washed successively with 1N HCl, saturated brine, saturated aqueous sodium bicarbonate and saturated brine and dried over anhydrous magnesium sulfate. After concentrating under vacuum, an excess of diazomethane in ether was added to the reaction mixture, and unreacted oleic acid was converted to methylester. The solvent was distilled off under vacuum, and the resulting crude product was purified by medium-pressure liquid column chromatography on silica gel to obtain the end compound (oil).

Instead of oleoyl chloride in ((a), a) palmitoyl chloride was used to obtain (a') palmitoyl-Pro-OMe (SUAM 1135).

(b) N-oleoyl-Leu-Pro-OMe (SUAM 1136)

H-Leu-Pro-OMe (1 equivalent) and TEA (1 equivalent) were dissolved in dry tetrahydrofurane, and oleoyl chloride (1 equivalent) was added dropwise under cooling with ice. The mixture was stirred at room temperature for 6 hours, and the hydrochloride of TEA which precipitated was filtered off. The solvent was distilled off under vacuum, and the resulting crude product was dissolved in a small amount of ether. The mixture was washed successively with 1N HCl, saturated brine, saturated aqueous sodium bicarbonate and saturated brine and dried over anhydrous magnesium sulfate. After concentrating under vacuum, an excess of diazomethane in ether was added, and unreacted oleic acid was converted to methylester. The solvent was distilled off under vacuum, and the resulting crude product was purified by medium-pressure liquid column chromatography on silica gel to obtain the end compound (oil).

Instead of oleoyl chloride in (b), (a) palmitoyl chloride, (b) stearoyl chloride and (c) linoleolyl chloride were used to obtain (a') palmitoyl-Leu-Pro-OMe (SUAM 1141), (b') stearoyl-Leu-Pro-OMe (SUAM 1142) and (c') linoleoyl-Leu-Pro-OMe (SUAM 1143), respectively. Further, instead of H-Leu-Pro-OMe in (b), (d) H-Val-Pro-OMe, (e) H-Ala-Pro-OMe (f) H-Leu-Leu-Pro-OMe, (g) H-Phe-Pro-OMe, (h) H-Met-Pro-OMe and (i) H-norLeu-Pro-OMe were used to obtain (d') oleoyl-Val-Pro-OMe (SUAM 1147), (e') oleoyl-Ala-Pro-OMe (SUAM 1076), (f') oleoyl-Leu-Leu-Pro-OMe (SUAM 1159), (g') oleoyl-Phe-Pro-OMe (SUAM 1194), (h') oleoyl-Met-Pro-OMe (SUAM 1198) and (i') oleoyl-norLeu-Pro-OMe (SUAM 1164), as oils, respectively.

Instead of H-Phe-Pro-OMe (1 equivalent) and TEA (1 equivalent) in (b), (c) H-Lys(Z)-Pro-OMe trifluoroacetate (1 equivalent) and TEA (2 equivalents) were used to obtain (c') oleoyl-Lys(Z)-Pro-OMe (SUAM 1197) as an oil, and (d) H-Glu(Bzl)-Pro-OMe trifluoroacetate (1 equivalent) and TEA (2-equivalents) were used to obtain (d') oleoyl-Glu(Bzl)-Pro-OMe (SUAM 1196) as an oil.

(c) N-oleoyl-Pro-Pro-OMe (SUAM 1195)

H-Pro-Pro-OMe (1 equivalent) and TEA (1 equivalent) were dissolved in dry tetrahydrofurane, and oleoyl chloride (1 equivalent) was added dropwise under cooling with ice. The mixture was stirred at room temperature for 6 hours, and the hydrochloride of TEA precipitated was filtered off. The solvent was distilled off under vacuum, and the resulting crude product was dissolved in a small amount of ether. The mixture was washed successively with 1N HCl, saturated brine, saturated aqueous sodium bicarbonate and saturated brine and dried over anhydrous magnesium sulfate. After concentrating under vacuum, an excess of diazomethane in ether was added, and unreacted oleic acid was converted to methylester. The solvent was distilled off under vacuum, and the resulting crude product was purified by medium-pressure liquid column chromatography on silica gel to obtain the end compound (oil).

EXAMPLE 2

(a) Oleoyl-Leu-Pro-CH$_2$OH (SUAM 1138)

Oleoyl-Leu-Pro-OMe (SUAM 1136) (2 g) obtained in Example 1 and sodiumborohydride (600 gm) were dissolved in t-butyl alcohol (60 ml), and the mixture was stirred under heating (80° C.). Then, absolute methanol (50 ml) was added dropwise under reflux. Thereafter, the mixture was refluxed under heating and stirring for two hours. After allowing the mixture to warm to room temperature, water (several ml) was added under cooling with ice, and unreacted sodiumborohydride was inactivated. Methanol and t-butyl alcohol were distilled off under vacuum and the residue was subjected to extraction with ethyl acetate. The extract was washed with saturated brine and dried over anhydrous magnesium sulphate. The solvent was distilled off under vacuum and the resulting crude product was purified by medium-pressure liquid column chromatography on silica gel to obtain the end compound as an oil (1 g).

Instead of oleoyl-Leu-Pro-OMe in (a), (a) oleoyl-Pro-OMe (SUAM 1131), (b) palmitoyl-Pro-OMe (SUAM 1135) (c) palmitoyl-Leu-Pro-OMe (SUAM 1141), (d) stearoyl-Leu-Pro-OMe (SUAM 1142), (e) linoleoyl-Leu-Pro-OMe (SUAM 1143), (f) oleoyl-Ala-Pro-OMe (SUAM 1076), (g) oleoyl-Val-Pro-OMe (SUAM 1147), (h) oleoyl-Leu-Leu-Pro-OMe (SUAM 1159), (i) oleoyl-Phe-Pro-OMe (SUAM 1194), (j) oleoyl-Met-Pro-OMe (SUAM 1198), (k) oleoyl-norLeu-Pro-OMe (SUAM 1164), (l) oleoyl-Lys(Z)-Pro-OMe (SUAM 1197) and (m) oleoyl-Glu(Bzl)-Pro-OMe were used as starting compounds to obtain (a') oleoyl-Pro-CH$_2$OH (SUAM 1133), (b') palmitoyl-Pro-CH$_2$OH (SUAM 1137), (c') palmitoyl-Leu-Pro-CH$_2$OH (SUAM 1144), (d') stearoyl-Leu-Pro-CH$_2$OH (SUAM 1145), (e') linoleoyl-Leu-Pro-CH$_2$OH (SUAM 1153), (f') oleoyl-Ala-Pro-CH$_2$OH (SUAM 1077), (g') oleoyl-Val-Pro-CH$_2$OH (SUAM 1151), (h') oleoyl-Leu-Leu-Pro-CH$_2$OH (SUAM 1152) (i') oleoyl-Phe-ProCH$_2$OH(SUAM 1205), (j') oleoyl-Met-Pro-CH$_2$OH (SUAM 1206), (k') oleoyl-norLeu-Pro-CH$_2$OH (SUAM 1165), (l') oleoyl-Lys(Z)-Pro-CH$_2$OH (SUAM 1207) and (m') oleoyl-Glu(CH$_2$OH)-Pro-CH$_2$OH (SUAM 1209) as oils, respectively.

(b) Oleoyl-Pro-Pro-CH₂OH (SUAM 1204)

Oleoyl-Pro-Pro-OMe (SUAM 1195) (2 g) obtained in Example 1 and sodiumborohydride (600 mg) were dissolved in t-butyl alcohol (60 ml), and the mixture was stirred under heating (80° C.) Then, absolute methanol (50 ml) was added dropwise under reflux. Thereafter, the mixture was refluxed under heating and stirring for two hours. After allowing the reaction solution to warm to room temperature, water (several ml) was added under cooling with ice, and unreacted sodiumborohydride was inactivated. methanol and t-butylalcohol were distilled off under vacuum and the residue was subjected to extraction with ethyl acetate. The extract was washed with saturated brine and dried over magnesium sulphate anhydride. The solvent was distilled off under vacuum and the resulting crude product was purified by medium-pressure liquid column chromatography on silica gel to obtain the end compound as an oil (1 g).

EXAMPLE 3

(a) Oleoyl-Leu-Pro-CHO (SUAM 1140)

Oleoyl-Leu-Pro-CH₂OH (SUAM 1138) (1 g) obtained in Example 2 and TEA (800 mg) were dissolved in dimethyl sulfoxide anhydride (8 ml), and sulfur tioxide-pyridine complex (700 mg) in dimethylsulfoxide (8 ml) was added under stirring. The mixture was stirred at room temperature for about 1 hour, and was then poured into ice water (100 ml). The reaction mixture was then subjected to extraction with ethyl acetate. The extract was washed successively with 10% citric acid solution, saturated brine, saturated aqueous sodium bicarbonate and saturated brine and dried over anhydrous magnesium sulfate. The solvent was distilled off under vacuum, and the resulting crude product was purified by medium-pressure liquid column chromatography on silica gel to obtain the end compound as an oil (700 mg).

Instead of oleoyl-Leu-Pro-CH OH (SUAM 1138) in (a), (a) oleoyl-Pro-CH₂OH (SUAM 1133), (b) palmitoyl-Pro-CH₂OH (SUAM 1137), (c) palmitoyl-Leu-Pro-CH₂OH (SUAM 1144), (d) stearoyl-Leu-Pro-CH₂OH (SUAM 1145), (e) linoleoyl-Leu-Pro-CH₂OH (SUAM 1153), (f) oleoyl-Ala-Pro-CH₂OH (SUAM 1077), (g) oleoyl-Val-Pro-CH₂OH (SUAM 1151), (h) oleoyl-Leu-Pro-CH₂OH (SUAM 1152), (i) oleoyl-Phe-Pro-CH OH (SUAM 1205), (j) oleoyl-Met-Pro-CH OH (SUAM 1206), (k) oleoyl-norLeu-Pro-CH₂OH (SUAM 1207), (l) oleoyl-Lys(Z)-Pro-CH₂OH (SUAM 1207) and (m) oleoyl-Glu(CH₂OH)-Pro-CH₂OH (SUAM 1209) were used as starting compounds to obtain (a') oleoyl-Pro-CHO (SUAM 1134), (b') palmitoyl-Pro-CHO (SUAM 1139), (c') palmitoyl-Leu-Pro-CHO (SUAM 1155), (d') stearoyl-Leu-Pro-CHO (SUAM 1154), (e') linoleoyl-Leu-Pro-CHO (SUAM 1157), (f') oleoyl-Ala-pro-CHO (SUAM 1092) (g') oleoyl-Val-Pro-CHO (SUAM 1156), (h') oleoyl-Leu-Leu-Pro-CHO (SUAM 1158), (i') oleoyl-Phe-Pro-CHO (SUAM 1212), (j') oleoyl-Met-Pro-CHO (SUAM 1214), (k') oleoyl-norLeu-Pro-CHO (SUAM 1166), (l') oleoyl-Lys(Z)-Pro-CHO (SUAM 1216) and (m') oleoyl-Glu(CHO)-Pro-CHO (SUAM 1217), respectively.

(b) Oleoyl-Pro-Pro-CHO (SUAM 1215)

Oleoyl-Pro-Pro-CH₂OH (SUAM 1204) (1 g) obtained in Example 2 and TEA (800 mg) were dissolved in anhydrous dimethylsulfoxide (8 ml), and sulfur trioxide-pyridine complex (700 mg) in dimethylsulfoxide (8 ml) was added under stirring. The mixture was stirred at room temperature for about 1 hour, and poured into ice water (100 ml). The reaction solution was subjected to extraction with ethyl acetate, and the extract was washed successively with 10% citric acid solution, saturated brine, saturated aqueous sodium bicarbonate and saturated brine and dried over anhydrous magnesium sulfate. The solvent was distilled off under vacuum, and the resulting crude product was purified by medium-pressure liquid column chromatography on silica gel to obtain the end compound as an oil (700 mg).

The analytical data for the compounds obtained are listed in Table 1. All the compouds in Table 1 are oils which are soluble in $CCl_4$, ether, $CHCl_3$, $CH_2Cl_2$, AcOEt and MeOH. SUAM 1194 is also soluble in benzene.

The present inventors examined the capability of the compounds of the present invention to inhibit the decomposition of Z-glycyl-prolyl-$\beta$-naphthylamide by prolyl endopeptidase and found that they exhibit strong anti-prolyl endopeptidase activity and yet show no inhibiting activity against proteinase such as papain, bromelain, trypsin, chymotrypsin, thermolysin and pepsin, as shown in the Experimental Examples described later.

The compounds thus obtained are novel and exhibit excellent effects against amnesia.

TABLE 1

| Ex. No. | Compound (SUAM number) | Molecular formula (molecular weight) | IR spectrum film (cm$^{-1}$) | Proton NMR spectrum $\delta$ (ppm) from TMS in CDCl$_3$ | $[\alpha]_D$ | EI-MS (m/z) |
|---|---|---|---|---|---|---|
| 1 (a) | oleoyl-L-Pro-OMe (SUAM-1131) | C$_{24}$H$_{43}$NO$_3$ (393.6) | | 0.8–1.0(3H,m), 1.1–2.4(32H, m), 3.60(2H,m), 3.70(3H,m), 4.26(1H,m), 5.32(2H,m) | | |
| 1 (a) | palmitoyl-L-Pro-OMe (SUAM-1135) | C$_{22}$H$_{41}$NO$_3$ (367.6) | | 0.8–1.0(3H,m), 1.1–2.4(32H, m), 3.60(2H,m), 3.70(3H,s), 4.24(1H,m) | | |
| 1 (b) | oleoyl-L-Leu-L-Pro-OMe (SUAM-1136) | C$_{30}$H$_{54}$N$_2$O$_4$ (506.8) | | 0.8–1.1(9H,m), 1.2–2.3(35H, m), 3.70(3H,s), 3.70(2H,m), 4.50(1H,m), 4.84(1H,m), 5.32(2H,m), 6.26(1H,d,J = 8) | | |
| 1 (b) | palmitoyl-L-Leu-L-Pro-OMe (SUAM-1141) | C$_{28}$H$_{52}$N$_2$O$_4$ (480.73) | | 0.8–1.1(9H,m), 1.1–2.4(35H, m), 3.70(2H,m), 3.72(3H,s), 4.50(1H,m), 4.84(1H,m), 6.25(1H,d,J = 8.2) | | |
| 1 (b) | stearoyl-L-Leu-L-Pro-OMe (SUAM-1142) | C$_{30}$H$_{56}$N$_2$O$_4$ (508.8) | | 0.8–1.0(9H,m), 1.1–2.3(37H, m), 3.60(4H,m), 3.66(3H,s), 4.42(1H,m), 4.78(1H,m), 6.26(1H,d,J = 8.2) | | |

TABLE 1-continued

| Ex. No. | Compound (SUAM number) | Molecular formula (molecular weight) | IR spectrum film (cm$^{-1}$) | Proton NMR spectrum δ (ppm) from TMS in CDCl$_3$ | $[\alpha]_D$ | EI-MS (m/z) |
|---|---|---|---|---|---|---|
| 1 (b) | linoleoyl-L-Leu-L-Pro-OMe (SUAM-1143) | $C_{30}H_{52}N_2O_4$ (504.8) | | 0.8–1.1(9H,m), 1.1–2.3(29H, m), 2.70(2H,m), 3.66(2H,m), 3.66(3H,s), 4.44(1H,m), 4.80(1H,m), 5.28(4H,m), 6.19(1H,d,J = 8) | | |
| 1 (b) | oleoyl-L-Val-L-Pro-OMe (SUAM-1147) | $C_{29}H_{52}N_2O_4$ (492.7) | | 0.86(3H,t,J = 6), 0.98(6H,dd, J = 9, J = 7), 1.1–2.3(33H,m), 3.70 (3H,s), 3.76(2H,m), 4.4–4.7(2H,m), 5.32(2H,m), | | |
| 1 (b) | oleoyl-L-Ala-L-Pro-OMe (SUAM-1076) | $C_{27}H_{48}N_2O_4$ (464.7) | 3300, 2920, 2840, 1740, 1630, 1530, 1450, 1190, 1170 | 0.88(3H,m), 1.30–2.18(35H,m), 3.70(3H,s), 3.58–3.81(2H,m), 4.51(1H,m), 4.76(1H,m), 5.30(2H,m), 6.72(1H,d,J = 9) | −54.9° C = 0.66 in CHCl$_3$ | 464 (M$^+$) |
| 1 (b) | oleoyl-L-Leu-L-Leu-Pro-OMe (SUAM-1159) | $C_{36}H_{65}N_3O_5$ (619.9) | | 0.8–1.0(15H,m), 1.1–2.4(38H, m), 3.70(2H,m), 3.72(3H,s), 4.50(2H,m), 4.74(1H,m), 5.32(2H,m), 5.88(1H,d,J = 8), 6.54(1H,d,J = 8) | | |
| 1 (b) | oleoyl-L-Phe-L-Pro-OMe (SUAM-1194) | $C_{33}H_{52}N_2O_4$ (540.8) | 3400, 3330, 3250, 2920, 2850, 1740, 1630, 1600, 1450, 1420, 1370, 1200, 1090, 980, 840, 770, 690, 590 | 0.9(3H,m), 1.0–2.4(34H,m), 3.70(2H,m), 3.76(3H,s) 4.50(1H,m), 5.00(1H,m), 5.35(2H,m), 6.40(1H,d,J = 9.0), 7.24(5H,s) | | |
| 1 (b) | oleoyl-L-Met-L-Pro-OMe (SUAM-1198) | $C_{29}H_{52}N_2O_4S$ (524.8) | 3300, 2920, 2850, 1740, 1630, 1530, 1440, 1360, 1270, 1190, 1170, 950, 720, 680 | 0.90(3H,m), 1.1–2.4(32H,m), 3.12(3H,s), 2.58(2H,m), 3.73(3H,s), 3.75(2H,m), 4.54(1H,m), 4.94(1H,m), 5.34(2H,m), 6.32(1H,d,J = 8.0) | | |
| 1 (b) | oleoyl-L-norLeu-L-Pro-OMe (SUAM-1164) | $C_{30}H_{54}N_2O_4$ (506.8) | | 0.8–1.0(6H,m), 1.0–2.4(38H, m), 3.70(2H,m), 3.72(3H,s), 4.50(1H,m), 4.76(1H,m), 5.32(2H,m), 6.28(1H,d,J = 8.0) | | |
| 1 (b) | oleoyl-L-Lys(Z)-L-Pro-OMe (SUAM-1197) | $C_{38}H_{61}N_3O_6$ (655.9) | 3300, 2920, 2850, 1740, 1710, 1630, 1530, 1450, 1240, 1190, 1170, 730, 690 | 0.90(3H,m), 1.1–2.4(38H,m), 3.22(2H,m), 3.66(3H,s), 3.72(2H,m), 4.50(1H,m), 4.80(1H,m), 5.10(2H,m), 5.35(2H,m), 6.34(1H,d,J = 8.0), 7.35(5H,s) | | |
| 1 (b) | oleoyl-L-Blu(Bzl)-L-Pro-OMe (SUAM-1196) | $C_{36}H_{55}N_2O_6$ (611.8) | 3300, 2920, 2850, 1730, 1630, 1450, 1170, 730, 690 | 0.90(3H,m), 1.0–2.8(36H,m), 3.70(2H,m), 3.72(3H,s), 4.50(1H,m), 4.90(1H,m), 5.14(2H,dd,J = 15.0), 5.35(2H,m), 6.38(H,d,J = 9.0) | | |
| 1 (c) | oleoyl-L-Pro-L-Pro-OMe (SUAM-1195) | $C_{29}H_{50}N_2O_4$ (490.7) | 3470, 2920, 2850, 1740, 1640, 1430, 1320, 1190, 1170, 720 | 0.90(3H,m), 1.2–2.4(36H,m), 3.4–4.0(4H,m), 3.72(3H,s), 4.5–4.8(2H,m), 5.35(2H,m) | | |
| 2 (a) | oleoyl-L-Leu-L-Pro-CH$_2$OH (SUAM-1138) | $C_{29}H_{54}N_2O_3$ (478.7) | | 0.8–1.1(9H,m), 1.2–2.3(35H, m), 3.6(3H,m), 3.9(1H,m), 4.2(1H,m), 4.54(1H,dd,J = 7, J = 4), 4.9(1H,m), 5.34(2H,m), 6.08(1H,d,J = 8) | | |
| 2 (a) | oleoyl-L-Pro-CH$_2$OH (SUAM-1133) | $C_{23}H_{43}NO_2$ (365.6) | | 0.8–1.0(3H,m), 1.1–2.4(32H, m), 3.48(2H,m), 3.62(2H,m), 4.20(1H,m), 5.18(1H,dd,J = 7, J = 4), 5.33(2H,m) | | |
| 2 (a) | palmitoyl-L-Pro-CH$_2$OH (SUAM-1137) | $C_{21}H_{41}NO_2$ (339.6) | | 0.8–1.0(3H,m), 1.1–2.4(32H, m), 3.4–3.8(4H,m), 4.20(1H,m), 5.18(1H,m) | | |
| 2 (a) | palmitoyl-L-Leu-L-Pro-CH$_2$OH (SUAM-1144) | $C_{27}H_{52}N_2O_3$ (452.7) | | 0.8–1.1(9H,m), 1.1–2.4(35H, m), 3.6(3H,m), 3.88(1H,m), 4.16(1H,m), 4.50(1H,dd,J = 7, J = 4), 4.82(1H,m), 6.06(1H,d,J = 8) | | |
| 2 (a) | stearoyl-L-Leu-L-Pro-CH$_2$OH (SUAM-1145) | $C_{29}H_{56}N_2O_3$ (480.8) | | 0.8–1.0(9H,m), 1.1–2.3(37H, m), 3.3–4.0(6H,m), 4.20(1H,m), 4.50(1H,m), 4.85(1H,m), 6.12(1H,d,J = 8) | | |
| 2 | linoleoyl-L- | $C_{29}H_{52}N_2O_3$ | | 0.8–1.0(9H,m), 1.1–2.4(29H, | | |

TABLE 1-continued

| Ex. No. | Compound (SUAM number) | Molecular formula (molecular weight) | IR spectrum film (cm$^{-1}$) | Proton NMR spectrum δ (ppm) from TMS in CDCl$_3$ | $[\alpha]_D$ | EI-MS (m/z) |
|---|---|---|---|---|---|---|
| (a) | Leu-L-Pro-CH$_2$OH (SUAM-1153) | (476.7) | | m), 2.72(2H,m), 3.3–3.7(3H, m), 3.90(1H,m), 4.16(1H,m), 4.56(1H,dd,J = 7, J = 4), 4.80(1H,m), 5.28(4H,m), 6.53(1H,d,J = 8) | | |
| 2 (a) | oleoyl-L-Ala-L-Pro-CH$_2$OH (SUAM-1077) | C$_{26}$H$_{48}$N$_2$O$_3$ (436.7) | 3400, 3300, 2920, 2840, 1620, 1530, 1450, 1040 | 0.88(3H,m), 1.29–2.19(35H, m), 3.59(4H,m), 4.20(1H,m), 4.51(1H,m), 4.74(1H,m), 5.31(2H,m), 6.68(1H,d,J = 9) | −29.4° c = 0.89 in CHCl$_3$ | 436 (M$^+$) |
| 2 (a) | oleoyl-L-Val-L-Pro-CH$_2$OH (SUAM-1151) | C$_{28}$H$_{52}$N$_2$O$_3$ (464.7) | | (CDCl$_3$ int TMS) 0.8–1.1(9H,m), 1.1–2.3(33H, m), 3.4–3.7(3H,m), 3.90(1H, m), 4.22(1H,m), 4.58(1H,m), 4.62(1H,dd,J = 10, J = 8), 5.33(2H,m), 6.14(1H,d,J = 9) | | |
| 2 (a) | oleoyl-L-Leu-L-Leu-L-Pro-CH$_2$OH (SUAM-1152) | C$_{35}$H$_{65}$N$_3$O$_4$ (591.9) | | (CDCl$_3$ int TMS) 0.8–1.0(15H,m), 1.1–2.3(38H, m), 3.4–3.9(4H,m), 4.26(1H, m), 4.50(2H,m), 4.80(1H,m), 5.34(2H,m), 5.84(1H,d,J = 8), 6.84(1H,d,J = 8) | | |
| 2 (a) | oleoyl-L-Phe-L-Pro-CH$_2$OH (SUAM-1205) | C$_{32}$H$_{52}$N$_2$O$_3$ (512.8) | 3400, 2920, 2850, 1610, 1540, 1440, 1040, 690 | 0.88(3H,m), 1.0–2.4(32H,m), 3.00(2H,m), 3.2–3.8(4H,m), 4.20(2H,m), 4.96(1H,m), 5.34(2H,m), 6.28(1H,d,J = 8.0), 7.26(5H,s) | | |
| 2 (a) | oleoyl-L-Met-L-Pro-CH$_2$OH (SUAM-1206) | C$_{22}$H$_{52}$N$_2$O$_3$S (423.7) | 3300, 2930, 2850, 1620, 1540, 1445, 1050, 730 | 0.90(3H,m), 1.0–2.4(34H,m), 2.10(3H,s), 2.54(2H,t,J = 7.0), 3.6–4.0(4H,m), 4.28(2H,m), 4.94(1H,m), 5.34(2H,m), 6.28(1H,d,J = 8.0) | | |
| 2 (a) | oleoyl-L-norLeu-L-Pro-CH$_2$OH (SUAM-1165) | C$_{29}$H$_{54}$N$_2$O$_3$ (478.7) | | 0.84(6H,m), 1.0–2.3(38H,m), 3.56(3H,m), 3.80(1H,m), 4.12(1H,m), 4.70(2H,m), 5.38(2H,m), 6.46(1H,d,J = 8.0) | | |
| 2 (a) | oleoyl-L-Lys(Z)-L-Pro-CH$_2$OH (SUAM-1207) | C$_{37}$H$_{61}$N$_2$O$_5$ (627.9) | 3300, 2925, 2850, 1700, 1620, 1530, 1450, 1250, 1050, 730, 700 | 0.88(3H,m), 1.0–2.3(38H,m), 3.18(2H,m), 3.4–3.8(3H,m), 4.30(2H,m), 4.6–5.2(3H,m), 5.08(2H,s), 5.32(2H,m), 6.38(1H,d,J = 8.0), 7.34(5H,s) | | |
| 2 (a) | oleoyl-L-Glu(CH$_2$OH)—L-Pro-CH$_2$OH (SUAM-1209) | C$_{28}$H$_{52}$N$_2$O$_4$ (480.7) | 3300, 2920, 1720, 2850, 1720, 1610, 1530, 1450, 1180 720, 590 | 0.82(3H,m), 1.0–2.2(36H,m), 3.2–3.9(7H,m), 4.12(1H,m), 4.76(2H,m), 5.28(2H,m), 7.04(1H,d,J = 8.0) | | |
| 2 (b) | oleoyl-L-Pro-L-Pro-CH$_2$OH (SUAM-1204) | C$_{28}$H$_{50}$N$_2$O$_3$ (462.7) | 3400, 2920, 2850, 1620, 1430, 1320, 1140, 920, 720 | 0.86(3H,m), 1.0–2.4(36H,m), 3.60(5H,m), 3.80–4.40(2H,m), 4.70(1H,m), 5.15(1H,m), 5.30(2H,m) | | |
| 3 (a) | oleoyl-L-Leu-L-Pro-CHO (SUAM-1140) | C$_{29}$H$_{52}$N$_2$O$_3$ (476.7) | 3300, 2920, 2825, 1730, 1620, 1540, 1440 | 0.8–1.1(9H,m), 1.2–2.3(35H, m), 3.7(2H,m), 4.52(1H,m), 4.85(1H,m), 5.34(2H,m), 6.19(1H,d,J = 8Hz), 9.50(1H,d,J = 2Hz) | $[\alpha]_D^{30}$ −27.9° c = 1.04 in CHCl$_3$ | 477 (M$^+$+1) |
| 3 (a) | oleoyl-L-Pro-CHO (SUAM-1134) | C$_{23}$H$_{41}$NO$_2$ (363.6) | 3300, 2920, 2850, 1725, 1640, 1420 | 0.8–1.0(3H,m), 1.1–2.4(32H,m), 3.54(2H,m), 4.24(1H,m), 5.33(2H,m), 9.51(1H,d,J = 2) | $[\alpha]_D^{30}$ −46.0° c = 1.00 in CHCl$_3$ | 364 (M$^+$+1) |
| 3 (a) | palmitoyl-L-Pro-CHO (SUAM-1139) | C$_{21}$H$_{39}$NO$_2$ (337.5) | 3350, 2910, 2850, 1720, 1630, 1430 | 0.8–1.0(3H,m), 1.1–2.4(32H,m), 3.56(2H,m), 4.24(1H,m), 9.52(1H,d,J = 2) | $[\alpha]_D^{30}$ −39.2° c = 1.53 in CHCl$_3$ | 338 (M$^+$+1) |
| 3 (a) | palmitoyl-L-Leu-L-Pro-CHO (SUAM-1155) | C$_{27}$H$_{50}$N$_2$O$_3$ (450.7) | 3300, 2920, 2850, 1730, 1620, 1540, 1440 | 0.8–1.1(9H,m), 1.2–2.4 (35H,m), 3.4–4.0(2H,m), 4.52(1H,m), 4.88(1H,m), 6.04(1H,d,J = 8), 9.52(1H,d,J = 1) | $[\alpha]_D^{30}$ −42.5° c = 1.70 in CHCl$_3$ | 451 (M$^+$+1) |
| 3 (a) | stearoyl-L-Leu-L-Pro-CHO (SUAM-1154) | C$_{29}$H$_{54}$N$_2$O$_3$ (478.8) | 3290, 2920, 2850, 1725, 1620, 1535, 1440 | 0.8–1.0(9H,m), 1.1–2.3 (37H,m), 3.5–3.8(4H,m), 4.40(1H,m), 4.80(1H,m), 6.77(1H,d,J = 8), 9.40(1H,d,J = 2) | $[\alpha]_D^{30}$ −41.9° c = 1.16 in CHCl$_3$ | 479 (M$^+$+1) |
| 3 (a) | linoleoyl-L-Leu-L-Pro-CHO (SUAM-1157) | C$_{29}$H$_{50}$N$_2$O$_3$ (474.7) | 3280, 2920, 2850, 1725, 1620, 1535, 1440 | 0.8–1.1(9H,m), 1.1–2.3(29H, m), 2.77(2H,m), 3.50(1H,m), 3.83(1H,m), 4.56(1H,m), 4.86(1H,m), 5.35(4H,m), | $[\alpha]_D^{30}$ −43.9° c = 1.03 in CHCl$_3$ | 475 (M$^+$+1) |

TABLE 1-continued

| Ex. No. | Compound (SUAM number) | Molecular formula (molecular weight) | IR spectrum film (cm$^{-1}$) | Proton NMR spectrum δ (ppm) from TMS in CDCl$_3$ | $[α]_D$ | EI-MS (m/z) |
|---|---|---|---|---|---|---|
| | | | | 6.02(1H,d,J = 8), 9.50(1H,d,J = 2) | | |
| 3 (a) | oleoyl-L-Ala-L-Pro-CHO (SUAM-1092) | C$_{26}$H$_{46}$N$_2$O$_3$ (434.7) | 3300, 2920, 2850, 2720, 1730, 1620, 1530, 1450 | 0.80(3H,m), 1.18-2.19(35H,m), 3.50(2H,m), 4.43(1H,m), 4.66(1H,m), 5.25(2H,m), 6.64(1H,d,J = 9), 9.40(1H,d,J = 1) | $[α]_D^{28}$ −35.1° c = 0.73 in CHCl$_3$ | 434 (M$^+$+1) |
| 3 (a) | oleoyl-L-Val-L-Pro-CHO (SUAM-1156) | C$_{28}$H$_{50}$N$_2$O$_3$ (462.7) | 3300, 2920, 2850, 1725, 1620, 1525, 1440 | 0.8-1.1(9H,m), 1.1-2.3(33H, m), 3.72(2H,m), 4.54(1H,m), 4.66(1H,dd,J = 9, J = 7), 5.34(2H,m), 6.08(1H,d,J = 8), 9.53(1H,d,J = 2) | $[α]_D^{30}$ −35.8° c = 1.47 in CHCl$_3$ | 463 (M$^+$+1) |
| 3 (a) | oleoyl-L-Leu-L-Leu-L-Pro-CHO (SUAM-1158) | C$_{35}$H$_{63}$N$_3$O$_4$ (589.9) | 3280, 2920, 2850, 1730, 1635, 1540, 1440 | 0.8-1.1(15H,m), 1.1-2.3 (38H,m), 3.3-4.0(2H,m), 4.50(2H,m), 4.80(1H,m), 5.34(2H,m), 5.80(1H,d,J = 8), 6.50(1H,d,J = 8), 9.50(1H,d,J = 2) | $[α]_D^{30}$ −92.8° c = 1.09 in CHCl$_3$ | 590 (M$^+$+1) |
| 3 (a) | oleoyl-L-Phe-L-Pro-CHO (SUAM-1212) | C$_{32}$H$_{50}$N$_2$O$_3$ (510.8) | 3300, 2920, 2850, 1730, 1620, 1530, 1450, 1100, 740, 700 | 0.88(3H,m), 1.0-2.4(32H,m), 3.08(2H,m), 3.60(2H,m), 4.38(1H,m), 5.00(1H,m), 5.32(2H,m), 6.24(1H,d,J = 8.0), 7.26(5H,s), 9.32(1H,d,J = 8.0) | | |
| 3 (a) | oleoyl-L-Met-L-Pro-CHO (SUAM-1214) | C$_{28}$H$_{50}$N$_2$O$_3$S (494.8) | 3300, 2920, 2850, 1730, 1620, 1530, 1440, 1340, 1110, 750 | 0.88(3H,m), 1.0-2.3(34H,m), 2.12(3H,s), 2.58(2H,m), 3.74(2H,m), 4.54(1H,m), 4.96(1H,m), 5.33(2H,m), 6.26(1H,d,J = 8.0), 9.50(1H,d,J = 2.0) | | |
| 3 (a) | oleoyl-L-norLeu-L-Pro-CHO (SUAM-1166) | C$_{29}$H$_{52}$N$_2$O$_3$ (476.7) | 3300, 2920, 2850, 1730, 1620, 1540, 1450, 1110, 990, 720 | 0.84(6H,m), 1.0-2.3(38H,m), 3.70(2H,m), 4.50(1H,m), 4.77(1H,m), 5.30(2H,m), 6.40(1H,d,J = 8.0), 9.47(1H,d,J = 2.0) | | |
| 3 (a) | oleoyl-L-Lys(Z)-L-Pro-CHO (SUAM-1216) | C$_{37}$H$_{59}$N$_3$O$_5$ (625.9) | 3310, 2930, 2850, 1710, 1620, 1530, 1450, 1340, 1250, 1130, 1020, 740, 700 | 0.88(3H,m), 1.0-2.4(38H,m), 3.20(2H,m), 4.54(1H,m), 4.82(2H,m), 5.08(2H,s), 5.32(2H,m), 6.26(1H,d,J = 8.0), 7.33(5H,s), 9.48(1H,d,J = 1.5) | | |
| 3 (a) | oleoyl-L-Glu(CHO)-L-Pro-CHO- (SUAM-1217) | C$_{28}$H$_{48}$N$_2$O$_4$ (476.7) | 3300, 2920, 2850, 1720, 1620, 1530, 1440, 1080 | 0.86(3H,m), 1.0-2.6(36H,m), 3.70(2H,m), 4.60(1H,m), 4.84(1H,m), 5.32(2H,m), 6.34(1H,d,J = 8.0), 9.50(1H,dd,J = 3.0, J = 1.0), 9.78(1H,d,J = 2.0) | | |
| 3 (b) | oleoyl-L-Pro-L-Pro-CHO (SUAM-1215) | C$_{28}$H$_{48}$N$_2$O$_3$ (460.7) | 3350, 2920, 2850, 1720, 1640, 1430, 1320, 1200, 750 | 0.86(3H,m), 1.0-2.4(36H,m), 3.60(4H,m), 4.60(2H,m), 5.32(2H,m), 9.50(1H,d,J = 2.0) | | |

EXAMPLE 4

Measurement of anti-prolyl endopeptidase activity

The method of Yoshimoto and Tsuru (T. Yoshimoto and D. Tsuru, Agr. Biol. Chem. 42, 2417, 1978) was used to measure the anti-prolyl endopeptidase activities of several compounds of the present invention. A mixture of 0.0025M Z-glycyl-proline-β-naphthylamide (0.25 ml), 0.1M phosphate buffer (pH, 7.0; 0.99 ml) and a solution of a particular anti-prolyl endopeptidase compound (0.01 ml) was incubated in a test tube at 37° C. for 3 minutes. Thereafter, 0.1 ml of a solution of prolyl endopeptidase (0.2 U/ml) was added and the mixture was heated at 35° C. for 10 minutes. After the reaction, 2.0 ml of Triton X-100 in 1M acetate buffer (pH, 4.0) was added to the reaction mixture until the final concentration of the surfactant was 10%. The mixture was left at room temperature for 15 minutes and the absorbance (a) at 410 nm was measured.

A sample for blind test was prepared by using the buffer instead of the anti-prolyl endopeptidase compound and its absorbance (b) was also measured. The percent inhibition of prolyl endopeptidase was calculated by the formula: $((b-a)/b) \times 100$, and the amount of a specific compound to achieve 50% inhibition (IC$_{50}$) was determined. The results are shown in Table 2.

TABLE 2

| Compound | IC$_{50}$ (ng/test tube) |
|---|---|
| SUAM 1155 | 0.7 |
| SUAM 1154 | 1.0 |
| SUAM 1158 | 80.0 |
| SUAM 1092 | 12.0 |
| SUAM 1156 | 0.7 |
| SUAM 1157 | 0.6 |
| SUAM 1140 | 0.8 |
| SUAM 1166 | 0.8 |
| SUAM 1212 | 0.4 |
| SUAM 1214 | 0.6 |
| SUAM 1216 | 0.6 |

TABLE 2-continued

| Compound | IC$_{50}$ (ng/test tube) |
|---|---|
| SUAM 1217 | 0.3 |
| SUAM 1215 | 0.3 |

EXAMPLE 5

Measurement of preventive effect against experimental amnesia caused in rats by scopolamine (intraperitoneal administration)

Several of the anti-prolyl endopeptidase compounds of the present invention were checked for their ability to prevent the inhibition of long-term memory fixation by scopolamine. Solutions of physiological saline (0.3 ml) that contained selected compounds of the present inventions in varying amounts (1 mg, 0.25 mg, 0.1 mg, 0.025 mg and 0.010 mg/kg) were administered intraperitoneally once a day to Wister male rats (100-120 g). One hour after the administration, electric shocks (1.7 mA) were applied to the rats so that they would acquire passive avoidance learning. Immediately thereafter, scopolamine was administered intraperitoneally to each rat in an amount of 3 mg per kg of body weight.

The result of the test was assessed both 24 hours and 48 hours after the administration of scopolamine. The number of amnesic rats and of sound rats was counted for each of the control group (rats to which the test compounds had not been administered but to which only scopolamine and physiological saline had been administered intraperitoneally and the treated group (rats to which both the test compound and scopolamine had been administered). The results are shown in Table 3.

TABLE 3

Amnesia test with rats (intraperitoneal administration)

| Sample | Drug administered after learning | No. of rats tested | Learning Initial avoidance time (sec.) | Learning No. of avoidance during learning | Learning time (sec.) | Avoidance time (sec.) 24 hrs. later | Avoidance time (sec.) 48 hrs. later | Pharmacological effects No. of amnesic rats/No. of rats tested | Pharmacological effects Percentage amnesia (%) |
|---|---|---|---|---|---|---|---|---|---|
| (1) physiological saline | physiological saline | 9 | 6.2 | 2.3 | 100 | 230.0 | 209.3 | 3/9 | 33 |
| (2) physiological saline | scopolamine (3 mg/kg · i.p.) | 10 | 2.7 | 2.9 | 100 | 90.6 | 110.4 | 8/10 | 80 |
| (3) SUAM 1156 (1 mg/kg · i.p.) | scopolamine (3 mg/kg · i.p.) | 10 | 3.5 | 2.8 | 100 | 184.0 | 119.8 | 5/10 | 50 |
| (4) SUAM 1156 (250 μg/kg · i.p.) | scopolamine (3 mg/kg · i.p.) | 10 | 2.1 | 2.8 | 100 | 240.6 | 226.0 | 2/10 | 20 |
| (5) SUAM 1156 (100 μg/kg · i.p.) | scopolamine (3 mg/kg · i.p.) | 10 | 1.8 | 1.6 | 100 | 300 | 276.4 | 1/10 | 10 |
| (6) SUAM 1140 (1 mg/kg · i.p.) | scopolamine (3 mg/kg · i.p.) | 5 | 9.4 | 1.6 | 100 | 73.0 | 103.0 | 3/5 | 60 |
| (7) SUAM 1140 (250 μg/kg · i.p.) | scopolamine (3 mg/kg · i.p.) | 5 | 1.7 | 2.4 | 100 | 263 | 284 | 1/5 | 20 |
| (8) SUAM 1140 (100 μg/kg · i.p.) | scopolamine (3 mg/kg · i.p.) | 5 | 3.1 | 1.8 | 100 | 300 | 300 | 0/5 | 0 |
| (9) SUAM 1140 (25 μg/kg · i.p.) | scopolamine (3 mg/kg · i.p.) | 5 | 2.2 | 2.0 | 100 | 300 | 300 | 0/5 | 0 |
| (10) SUAM 1140 (10 μg/kg · i.p.) | scopolamine (3 mg/kg · i.p.) | 5 | 4.7 | 2.0 | 100 | 185.0 | 189.0 | 2/5 | 40 |
| (11) SUAM 1158 (100 μg/kg · i.p.) | scopolamine (3 mg/kg · i.p.) | 10 | 2.8 | 3.0 | 100 | 300 | 300 | 0/10 | 0 |
| (12) SUAM 1158 (25 μg/kg · i.p.) | scopolamine (3 mg/kg · i.p.) | 10 | 1.7 | 2.3 | 100 | 300 | 300 | 0/10 | 0 |
| (13) SUAM 1155 (100 μg/kg · i.p.) | scopolamine (3 mg/kg · i.p.) | 10 | 2.2 | 3.0 | 100 | 300 | 300 | 0/10 | 0 |
| (14) SUAM 1154 (100 μg/kg · i.p.) | scopolamine (3 mg/kg · i.p.) | 10 | 4.7 | 2.0 | 100 | 300 | 300 | 0/10 | 0 |
| (15) SUAM 1214 (1 mg/kg · i.p.) | scopolamine (3 mg/kg · i.p.) | 10 | 9.5 | 1.6 | 100 | 73.0 | 103.0 | 6/10 | 60 |
| (16) SUAM 1214 (250 μg/kg · i.p.) | scopolamine (3 mg/kg · i.p.) | 10 | 2.1 | 2.8 | 100 | 240.6 | 226.0 | 2/10 | 20 |
| (17) SUAM 1214 (100 μg/kg · i.p.) | scopolamine (3 mg/kg · i.p.) | 10 | 1.8 | 1.6 | 100 | 300 | 276.4 | 1/10 | 10 |
| (18) SUAM 1214 (25 μg/kg · i.p.) | scopolamine (3 mg/kg · i.p.) | 10 | 2.2 | 2.0 | 100 | 300 | 300 | 0/10 | 0 |
| (19) SUAM 1214 (10 μg/kg · i.p.) | scopolamine (3 mg/kg · i.p.) | 10 | 4.6 | 1.9 | 100 | 300 | 300 | 0/10 | 0 |
| (20) SUAM 1166 (25 μg/kg · i.p.) | scopolamine (3 mg/kg · i.p.) | 10 | 3.7 | 2.1 | 100 | 300 | 300 | 0/10 | 0 |
| (21) SUAM 1212 (25 μg/kg · i.p.) | scopolamine (3 mg/kg · i.p.) | 10 | 2.7 | 2.4 | 100 | 300 | 285 | 0/10 | 0 |
| (22) SUAM 1215 (25 μg/kg · i.p.) | scopolamine (3 mg/kg · i.p.) | 10 | 3.2 | 1.8 | 100 | 300 | 300 | 0/10 | 0 |
| (23) SUAM 1215 (10 μg/kg · i.p.) | scopolamine (3 mg/kg · i.p.) | 10 | 2.2 | 2.4 | 100 | 300 | 300 | 0/10 | 0 | i.p. intraperitoneal administration

SUAM 1156 exhibited no remarkable effect when administered orally in an amount of 1 mg/kg, but exhibited a considerably excellent anti-amnesic action when administered orally in an amount of 0.1 mg/kg. Although SUAM 1140 and SUAM 1214 exhibited no remarkable effect when administered orally in an amount of 1 mg/kg, they exhibited a considerably excellent anti-amnesic action when administered orally in amounts of 0.1 mg/kg and 0.025 mg/kg, respectively. SUAM 1214 exhibited a remarkable anti-amnesic action even when the dose was lowered to 0.01 mg/kg. SUAM 1158, 1155 and 1154 exhibited a strong anti-amnesic action when administered orally in an amount of 0.1 mg/kg. SUAM 1158 exhbited excellent effect even at a dose of 0.025 mg/kg. In addition, SUAM 1166, 1212 and 1215 also exhibited a strong anti-amnesic action when administered orally in an amount of 0.025 mg/kg. SUAM 1215 exhibited a strong anti-amnesic action even at a dose of 0.01 mg/kg. The action of all the compounds depends upon the dose.

EXAMPLE 6

Anti-hypoxia action

The compounds of the present invention were checked for their anti-hypoxia action in ddY strain male mice (body weight: 25–34 g). Each of the treated groups consisted of 7 to 10 mice. Test samples were prepared by adding 2 to 3 drops of Tween 80 ® to physiological saline and suspending the respective compounds in the saline. The so conditioned test samples were administered (0.1 m 10 g) to each of the mice used.

At 30 minutes after the administration, each of the mice was placed in a desiccator having a volume of 1 l, and the desiccator was evacuated to 180 mmHg using a vacuum pump. The period of time from the start of the evacuation until the arrest of breathing was defined as Survival Time (minute).

When a mouse survived for 15 minutes or more, the survival time was recorded as being 15 minutes. Student's t-test was employed for significance analysis.

The results are shown in Table 4 below.

gelatin, tragacanth, methyl cellulose and polyvinyl pyrrolidone. Examples of disintegrator are starch and agar etc.

The active ingredient (I) of the agent of the invention is orally administered to an adult patient in a dose of 10 to 4,000 mg, preferably 100 to 1,000 mg/day, or administered parenterally in a dose of 1 to 2,000 mg, preferably 50 to 500 mg/day. The dose may be varied depending on the disease, age, weight, or condition of the patient or the formulation of the drugs.

| Formulation 1 | |
|---|---|
| Ingredient | Part |
| Compound of the formula (I) | 10 |
| Lactose | 75 |
| Magnesium oxide (MgO >96%) | 15 |

The ingredients are mixed thoroughly, and tablests or capsules are formulated from the mixture.

| Formulation 2 | |
|---|---|
| Ingredient | Part |
| Compound of the formula (I) | 45 |
| Starch | 15 |
| Lactose | 40 |

The above ingredients are mixed thoroughly, and powders or fine granules are formulated from the mixture.

| Formulation 3 | |
|---|---|
| Ingredient | Part |
| Compound of the formula (I) | 1 |
| Surface active agent | 5 |
| Physiological saline | 94 |

The above ingredients are mixed under heating, and dispensed under sterile conditions into ampoules to obtain injections.

TABLE 4

| Compound | Chemical structure | Dose (mg/kg. i.p.) | No. of survival/used | | Survival time (mini Mean ± S.E.) | | Ratio |
|---|---|---|---|---|---|---|---|
| | | | Control | Drug | Control | Drug | |
| SUAM 1212 | 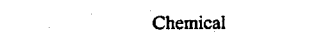 | 1 | 0/10 | 0/7 | 2.32 ± 0.11 | 2.94 ± 0.27* | 1.27 |
| | | 10 | 0/10 | 0/7 | 2.25 ± 0.15 | 2.89 ± 0.29# | 1.28 |

*p < 0.05
p < 0.1

The present invention also relates to an anti-amnesic agent useful for the treatment of diseases originating from organic disorders in the brain. The anti-amnesic agent comprises at least one compound of the formula (I) together with a pharmaceutically acceptable carrier.

The formulation of the agent of the invention includes either solid formulations such as capsules, tablets and powders, a liquid formulations such as elixirs, syrups and suspensions for oral administration. Alternatively, the active compounds (I) may be formulated as injections or suppositories.

The carrier included in the agent of the invention may be selected from pulverulent solid carriers such as lactose, saccharose, dextrose, mannitol, sorbitol, cellulose, and glycine etc.

The agent of the invention may further contain a lubricant, a binder or a disintegrater. Examples of lubricant are silicon dioxide, talc, magnesium stearate and polyethylene glycol. Examples of binder are starch,

What is claimed is:

1. A dipeptide derivative of fatty acid of formula (I)

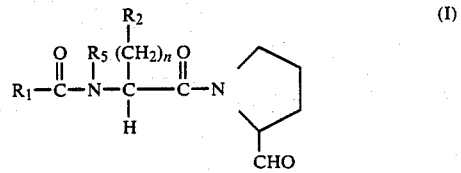

(wherein n is a number of 0 to 12; $R_1$ is a saturated or unsaturated unbranched hydrocarbon group having 5 to 25 carbon atoms (the unsaturated carbon chain may include a plurality of double bonds); $R_2$ represents, when n is 0, an unbranched or branchd alkyl group having 1 to 5 carbon atoms, whereas, when n is an integer of 1 to 12, $R_2$ is methyl group, phenyl group, hydroxyphenyl group, carboxyl group, formyl group, amino group, hydroxyl group or methylthio group (these groups may be substituted); $R_5$ is hydrogen atom, or when n is 3, $R_2$ and $R_5$ together may represent a single bond between carbon atom and nitrogen atom).

2. A compound according to claim 1, represented by the formula (Ia):

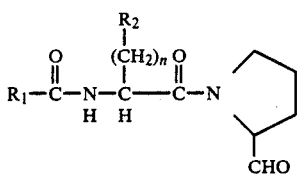

(Ia)

(wherein n is an integer of 1 to 12; $R_1$ represents the meaning given in claim 1; $R_2$ is methyl group, phenyl group, hydroxyphenyl group, carboxyl group, formyl group, amino group, hydroxyl group or methylthio group (these groups may be substituted)).

3. A compound according to claim 1, represented by the formula (Ib):

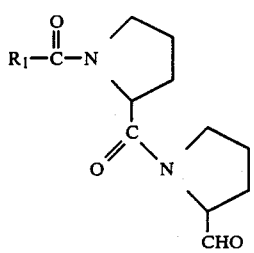

(Ib)

(wherein $R_1$ represents the meaning given in claim 1).

4. A compound according to claim 1, represented by the formula (Ic):

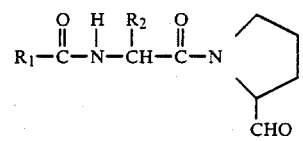

(Ic)

(wherein m, $R_1$ represents the meaning given in claim 1; $R_2$ is:

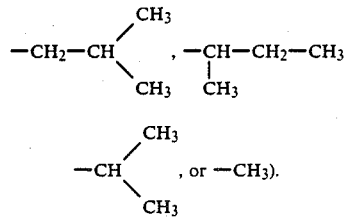

5. A compound according to either one of claims 1 and 2, wherein n represents a number of 1 to 6.

6. An anti-amnesic agent containing, as an active ingredient, dipeptide derivative of fatty acid of formula (I):

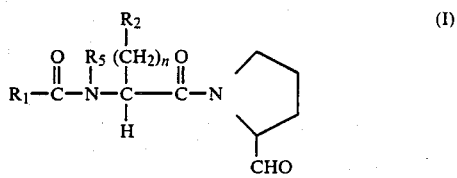

(I)

(wherein n is a number of 0 to 12; $R_1$ is a saturated or unsaturated unbranched hydrocarbon group having 5 to 25 carbon atoms (the unsaturated carbon chain may include a plurality of double bonds); $R_2$ represents, when n is 0, an unbranched or branched alkyl group having 1 to 5 carbon atoms, whereas, when n is an integer of 1 to 12, $R_2$ is methyl group, phenyl group, hydroxyphenyl group, carboxyl group, formyl group, amino group, hydroxyl group or methylthio group (these groups may be substituted); $R_5$ is hydrogen atom, or when n is 3, $R_2$ and $R_5$ together may represent a single bond between carbon atom and nitrogen atom), together with a pharmaceutically acceptable carrier.

* * * * *